United States Patent [19]

Lange, III et al.

[11] Patent Number: 5,624,836
[45] Date of Patent: Apr. 29, 1997

[54] DNA ENCODING BOVINE PANCREATIC CHOLESTEROL ESTERASE

[76] Inventors: Louis G. Lange, III, 38 Kingsbury Pl., St. Louis, Mo. 63112; Curtis A. Spilburg, 2230 Willow Ridge La., Chesterfield, Mo. 63017

[21] Appl. No.: 462,884

[22] Filed: Jun. 5, 1995

Related U.S. Application Data

[62] Division of Ser. No. 350,501, Dec. 6, 1994, which is a continuation of Ser. No. 856,910, filed as PCT/US90/06483, Nov. 13, 1990, abandoned, which is a continuation of Ser. No. 434,899, Nov. 13, 1989, Pat. No. 5,173,408.

[51] Int. Cl.$^6$ ............................... C12N 9/20; C12N 15/55
[52] U.S. Cl. ...................... 435/325; 435/252.3; 435/198; 435/320.1; 435/348; 435/419; 435/358; 536/23.2
[58] Field of Search ........................ 435/198, 320.1, 435/240.1, 240.2, 240.4, 252.3; 536/23.2

[56] References Cited

U.S. PATENT DOCUMENTS

| | | | |
|---|---|---|---|
| 4,732,757 | 3/1988 | Stolle et al. | 424/87 |
| 4,944,944 | 7/1990 | Tang et al. | 424/94.6 |
| 5,017,565 | 5/1991 | Lange, III et al. | 514/54 |
| 5,063,210 | 11/1991 | Lange, III et al. | 514/54 |
| 5,173,408 | 12/1992 | Lange, III et al. | 435/69.1 |
| 5,200,183 | 4/1993 | Tang et al. | 424/94.6 |
| 5,210,183 | 5/1993 | Lindahl et al. | 530/350 |
| 5,352,601 | 10/1994 | Lange, III et al. | 435/196 |
| 5,432,058 | 7/1995 | Lange, III et al. | 435/11 |

FOREIGN PATENT DOCUMENTS 9012579 11/1993 European Pat. Off. ..... A61K 31/725

OTHER PUBLICATIONS

Kyger et al., *Biochemical and Biophysical Research Communications*, 164(3): 1302–1309 (1989).
Custer et al., *Am. J. Physiol.*, 266: F767–F774 (1994).
Bosner et al., *Proc. Natl. Acad. Sci. USA*, 85: 7438–7442 (1988).
Vahouny et al., *Proc. J. Exp. Biol. Med.*, 116: 496 (1964).
Casdorph, Richard H., Cholestyramine and Ion–Exchange Resins, pp. 221–256, 1976.
Wagner, Richard W., *Nature*, 372: 333–335 (1994).
Ullrich et al., *The EMBO Journal*, 3(2): 3621–4 (1984).
Werner et al., *J. Biol. Chem.*, 269: 6637–6639 (1994).
Abouakil et al., *Biochemica et Biophysica Acta*, 961: 299–308 (1988).
Han et al., *Biochemistry*, 26: 1617–25 (1987).
Neckers et al., *Am. J. Phyusiol*, 265: L1–L12 (1993).
Stoll et al., *Biochem. J.*, 180: 465–470 (1979).
Labow et al., *Arch. Biochem. Biophys. Acta*, 749: 32–41 (1975).
Brown et al., *Biochem. Biophys. Acta*, 769: 471–478 (1984).
Rudd et al., *Biochemica et Biophysica Acta*, 918: 106–114 (1987).
Jaye et al., *Nucleic Acids Research*, 11(8): 2325–2335 (1983).
Cossum et al., *J. Pharmacol. Exper. Therapeutics*, 267: 1181–1190 (1993).
Fitzpatrick et al., *Journal of Virology* 62(11): 4239–4248 (1988).
Cohen, Jack S., *Advances in Pharmacology*, 25: 319–339 (1994).
Tenenhouse et al., *J. Clin. Invest.*, 93: 671–676 (1994).
Gao et al., *Molec. Pharacol.*, 43: 45–50 (1993).
Emtage et al., *Proc. Natl. Acad. Sci. USA*, 80: 3671–75 (1983).
Dean et al., *Proc. Natl. Acad. Sci. USA*, 91: 11762–11766 (1994).
Leonetti et al., *Proc. Natl. Acad. Sci. USA*, 88: 2702–2706 (1991).
Yakubov et al., *Proc. Natl. Acad. Sci. USA*, 86: 6454–6458 (1989).
Zamecnik et al., *Proc. Natl. Acad. Sci. USA* 91: 3156–3160 (1994).
Magagnin et al., *Proc. Natl. Acad. Sci. USA*, 90: 5979–5983 (1993).
Agrawal et al., *Proc. Natl. Acad. Sci. USA*, 88: 7595–7599 (1991).
Morishita et al., *Proc. Natl. Acad. Sci. USA*, 90: 8474–8478 (1993).
Ratajczak et al., *Proc. Natl. Acad. Sci. USA*, 89: 11823–11827 (1992).
Towbin et al., *Proc. Natl. Acad. Sci. USA*, 76: 4350–4354 (1979).
Stein et al., *Science*, 261: 1004–1012 (1993).
Laemmli, U.K., *Nature*, 227: 680–685 (1970).
Simons et al., *Nature*, 359: 67–70 (1992).
Allain et al., *Clin. Chem.*, 20: 470 (1974).

*Primary Examiner*—Keith D. Hendricks
*Attorney, Agent, or Firm*—McDonnell Boehnen Hulbert & Berghoff

[57] ABSTRACT

The invention provides methods for the purification to homogeneity of pancreatic cholesterol esterase in useful quantities from a variety of mammalian species. The gene for a mammalian pancreatic cholesterol esterase has been cloned and sequenced, and is useful for expressing cholesterol esterase in a transformed eukaryotic or prokaryotic cell culture. Thus, methods according to the invention enable the production of large quantities of pancreatic cholesterol esterase for the screening of inhibitors, the production of antibodies, and for commercial purposes related to the alteration of cholesterol/cholesterol ester composition of materials containing free or esterified cholesterol.

6 Claims, 7 Drawing Sheets

FIG. 1

```
        10          20          30          40          50
LGASRLGPSP  GCLAVASAAK  LGSVYTEGGF  VEGVNKKLSL  FGDSVDIFKG
        60          70          80          90         100
IPFAAAPKAL  EKPERHPGWQ  GTLKAKSFKK  RCLQATLTQD  STYGNEDCLY
       110         120         130         140         150
LNIWVPQGRK  EVSHDLPVMI  WIYGGAFLMG  ASQGANFLSN  YLYDGEEIAT
       160         170         180         190         200
RGNVIVVTFN  YRVGPLGFLS  TGDSNLPGNY  GLWDQHMAIA  WVKRNIEAFG
       210         220         230         240         250
GDPDNITLFG  ESAGGASVSL  QTLSPYNKGL  IKRAISQSCV  GLCPWAIQQD
       260         270         280         290         300
PLFWAKRIAE  KVGCPVDDTS  KMAGCLKITD  PRALTLAYKL  PLGSTEYPKL
       310         320         330         340         350
HYLSFVPVID  GDFIPDDPVN  LYANAADVDY  IAGTNDMDGH  LFVGMDVPAI
       360         370         380         390         400
NSNKQDVTEE  DFYKLVSGLT  VTKGLRGANA  TYEVYTEPWA  QDSSQETRKK
       410         420         430         440         450
TMVDLETDIL  FLIPTKIAVA  QHKSHAKSAN  TYTYLFSQPS  RMPIYPKWMG
       460         470         480         490         500
ADHADDLQYV  FGKPFATPLG  YRAQDRTVSK  AMIAYWTNFA  RTGDPNTGHS
       510         520         530         540         550
YVPANWDPYT  LEDDNYLEIN  KQMDSNSMKL  HLRTNYLQFW  TQTYQALPTV
       560         570         580         590
TSAGASLLPP  EDNSQASPVP  PADNSGAPTE  PSAGDSEVAQ  MPVVIGF
```

FIG. 2a

```
                              10         20
                     GCCTAGAGGC AGACACTCAC TATGGGGCG
        * 10       * 20       * 30       * 40       * 50
     GCTGGGAGCT AGCCGTCTTG GGCCGTCGCC TGGCTGCTTG GCAGTAGCGA
     30         40         50         60         70
     cCTGGAgGtT CTGTTTCT-T GGC-cTCACC -TGCTGCTTG GCAGcTGCTT

* 60       * 70       * 80       * 90       * 100
     GTGCAGCGAA GTTGGGCTCC GTATACACCG AAGGCGGCTT CGTGGAGGGC
     80         90         100        110        120
     GTGCTGCAAA GTTGGGTGCT cTGTACACAG AAGGCGGtTT TGTGGAGGGC

* 110      * 120      * 130      * 140      * 150
     GTCAACAAGA AGCTGAGCCT CTTTGGCGAC TCTGTTGACA TCTTCAAGGG
                                TGG
     130        140        :          160        170        180
     GTCAACAAGA AACTCAGTCT CTGTGGTGAC TCTGTTGACA TCTTCAAGGG

* 160      * 170      * 180      * 190      * 200
     CATCCCCTTC GCTGCCGCCC CCAAGGCCCT GGAGAAGCCC GAGCGACACC
     190        200        210        220
     CATCCCCTTC GCTACC---G CCAAGACCCT GGAGAATCCT cAGCGTCACC

* 210      * 220      * 230      * 240      * 250
     CCGGCTGGCA AGGGACCCTG AAGGCCAAGA GCTTTAAGAA ACGGTGCCTG
                                   A
     230        240        250 :      260        270
     CTGGCTGGCA AGGGACACTG AAGGCTCAG- ACTTcAAGAA ACGATGTCTA

* 260      * 270      * 280      * 290      * 300
     CAGGCCACGC TCACGCAGGA CAGCACCTAC GGAAATGAAG ACTGCCTCTA
     280        290        300        310        320
     CAAGCCACCA TCACCCAGGA TGATACCTAT GGGCAAGAAG ACTGCCTCTA

* 310      * 320      * 330      * 340      * 350
     CCTCAACATC TGGGTCCCCC AGGGCAGGAA GGAAGTCTCC CACGACCTGC
     330        340        350        360        370
     TCTCAACATC TGGGTCCCTC AGGGCAGGAA GcAAGTGTCT CATGACCTGC
```

FIG. 2b

```
          * 360       * 370       * 380       * 390       * 400
         CCGTCATGAT  CTGGATCTAT  GGAGGCGCCT  TCCTCATGGG  GGCCAGCCAA
          380         390         400         410         420
         CTGTGATGGT  CTGGATCTAT  GGAGGTGCCT  TCCTCATGGG  GTCTGGCCAG

* 410       * 420       * 430       * 440       * 450
         GGGGCCAACT  TTCTCAGCAA  CTACCTCTAC  GACGGGGAGG  AGATTGCCAC
          430         440         450         460         470
         GGAGCCAATT  TTCTCAAGAA  TTACCTGTAT  GATGGGGAAG  AGATCGCCAC

* 460       * 470       * 480       * 490       * 500
         ACGGGGCAAC  GTCATCGTGG  TCACGTTCAA  CTACCGCGTT  GGGCCCCTGG
          480         490         500         510         520
         TAGAGCCAAT  GTCATTGTGG  TCACCTTCAA  CTACCGTGTC  GGACCCTTGG

* 510       * 520       * 530       * 540       * 550
         GCTTTCTCAG  CACCGGGGAC  TCCAACCTGC  CAGGTAACTA  TGGCCTTTGG
          530         540         550         560         570
         GTTTCCTTAG  CACCGGAGAT  GCTAACCTTC  CAGGTAACTT  TGGACTTCGA

* 560       * 570       * 580       * 590       * 600
         GATCAGCACA  TGGCCATTGC  TTGGGTGAAG  AGGAACATTG  AGGCCTTCGG
          580         590         600         610         620
         GATCAGCACA  TGGCTATTGC  CTGGGTGAAG  AGGAACATTG  CAGCCTTTGG

* 610       * 620       * 630       * 640       * 650
         AGGAGACCCC  GACAACATCA  CCCTCTTTGG  GGAGTCGGCC  GGAGGCGCCA
          630         640         650         660         670
         AGGAGACCCC  GATAACATCA  CCATCTTTGG  GGAATCTGCT  GGAGGTGCCA

* 660       * 670       * 680       * 690       * 700
         GCGTCTCTCT  GCAGACCCTC  TCTCCCTACA  ACAAGGGCCT  CATCAAGCGA
```

FIG. 2c

```
      680         690         700         710         720
   TTGTCTCTCT GCAGACCCTC TCcCCATACA ACAAGGGCCT CATCcGGCGA
     * 710      * 720      * 730      * 740      * 750
   GCCATCAGCC AGAGTGGAGT GGGTTTGTGC CCTTGGGCCA TCCAGCAGGA
      730         740         750         760         770
   GCCATCAGTC AGAGTGGTGT GGcAcTGAGC CCcTGGGCCA TCCAGgAGAA
     * 760      * 770      * 780      * 790      * 800
   CCCCCTCTTC TGGGCTAAAA GGATTGCAGA GAAGGTGGGC TGCCCCGTGG
      780         790         800         810         820
   TCCACTTTTC TGGGCcAAAA cGATcGCTAA GAAGGTGGGA TGCCCCAcAG
     * 810      * 820      * 830      * 840      * 850
   ACGACACCAG CAAGATGGCT GGGTGTCTGA AGATCACTGA .CCCCCGTGCC
      830         840         850         860         870
   ATGATACCGc CAAGATGGCT GGGTGTCTGA AGATCACAGA TCCCCGAGCC
     * 860      * 870      * 880      * 890      * 900
   CTGACGCTGG CCTATAAGCT GCCCCTGGGA AGCACGGAAT ACCCCAAGCT
      880         890         900         910         920
   TTGACACTGG CCTAcAgGtT GCCCTTGAAA AGCcAGGAGT ACCCCATTGT
     * 910      * 920      * 930      * 940      * 950
   GCACTATCTG TCCTTCGTCC CCGTCATCGA TGGAGACTTC ATCCCTGATG
      930         940         950         960         970
   GCACTAcCTG gCCTTCATCC CTGTCGTCGA TGGTGACTTC ATTCCTGATG
     * 960      * 970      * 980      * 990      * 1000
   ACCCCGTCAA CCTGTACGCC AACGCCGCGG ACGTCGACTA CATAGCGGGC
      980         990         1000        1010        1020
   ATCCCATCAA CCTGTACGAC AACGCTGCTG ACATTGACTA CTTAGCGGGT
```

FIG. 2d

```
          *1010       *1020       *1030       *1040       *1050
       ACCAATGACA  TGGACGGCCA  CCTCTTTGTC  GGGATGGACG  TGCCAGCCAT
       1030        1040        1050        1060        1070
       ATTAATGACA  TGGATGGCCA  CCTGTTTGCT  ACAGTTGACG  TGCCCGCCAT

*1060       *1070       *1080       *1090       *1100
       CAACAGCAAC  AAACAGGACG  TCACGGAGGA  GGACTTCTAT  AAGCTGGTCA
       1080        1090        1100        1110        1120
       CGACAAGGCC  AAGCAGGATG  TCACAGAGGA  GGACTTCTAC  AGGCTAGTCA

*1110       *1120       *1130       *1140       *1150
       GCGGGCTCAC  CGTCACCAAG  GGGCTCAGAG  GTGCCAATGC  CACGTACGAG
       1130        1140        1150        1160        1170
       GTGGACACAC  TGTCGCCAAG  GGGCTTAAAG  GCACCCAAGC  CACCTTTGAC

*1160       *1170       *1180       *1190       *1200
       GTGTACACCG  AGCCCTGGGC  CCAGGACTCA  TCCCAGGAGA  CCAGGAAGAA
       1180        1190        1200        1210        1220
       ATCTACACTG  AGTCCTGGGC  CCAGGACCCG  TCCAGGAGA   ACATGAAGAA

*1210       *1220       *1230       *1240       *1250
       GACCATGGTG  GACCTGGAGA  CTGACATCCT  CTTCCTGATC  CCCACAAAGA
       1230        1240        1250        1260        1270
       GACAGTGGTG  GCCTTTGAGA  CTGACATACT  CTTCCTGATC  CCCACAGAGA

*1260       *1270       *1280       *1290       *1300
       TTGCCGTGGC  CCAGCACAAG  AGCCACGCCA  AGAGCGCCAA  CACCTACACC
                                    G
       1280        1290        :           1310        1320
       TGGCTCTGGC  CCAGCA-CAG  ACCCATGCCA  AGAGTGCCAA  GACCTACTCT

*1310       *1320       *1330       *1340       *1350
       TACCTGTTCT  CCCAACCGTC  TCGGATGCCC  ATCTACCCCA  AGTGGATGGG
```

FIG. 2e

```
 1330       1340       1350       1360       1370
TACCTGTTtT CCCAcCCtTC ACGaATGCCt ATCTACCCaA AATGGATGGG

*  1360    *  1370    *  1380    *  1390    *  1400
   *          *          *          *          *
GGCTGACCAC GCCGATGACC TCCAGTATGT CTTCGGGAAG CCCTTCGCCA
 1380       1390       1400       1410       1420
GGCAGACCAC GCTGATGACC TCCAGTAcGT CTTTGGGAAG CCCTTTGCCA

*  1410    *  1420    *  1430    *  1440    *  1450
   *          *          *          *          *
CCCCCCTGGG CTACCGGGCC CAAGACAGGA CTGTCTCCAA GGCCATGATT
 1430       1440       1450       1460       1470
CCCCACTGGG CTACCGGGCC CAAGACAGGA CTGTCTCCAA GGCCATGATT

*  1460    *  1470    *  1480    *  1490    *  1500
   *          *          *          *          *
GCCTACTGGA CCAACTTTGC CAGAACTGGG GACCCTAACA CGGGCCACTC
 1480       1490       1500       1510       1520
GCCTACTGGA CCAACTTTGC CAaGAgTGGG GACCCcAACA TGGGCAACTC

*  1510    *  1520    *  1530    *  1540    *  1550
   *          *          *          *          *
GACAGTGCCC GCAAACTGGG ATCCCTACAC CCTGGAAGAT GACAACTACC
 1530       1540       1550       1560       1570
AcCcGTGCCC ACAcACTGGT AcCCtTAtAC CATGGAgAAT GGtAACTACC

*  1560    *  1570    *  1580    *  1590    *  1600
   *          *          *          *          *
TGGAAATCAA CAAGCAGATG GACAGCAACT CTATGAAGCT GCATCTGAGG
 1580       1590       1600       1610       1620
TGGAcATCAA TAAGAAaATa AcCAGCAcCT CcATGAAGGa GCAcCTAAGG

*  1610    *  1620    *  1630    *  1640    *  1650
   *          *          *          *          *
ACCAACTACC TGCAGTTCTG GACCCAGACC TACCAGGCCC TGCCCACGGT
 1630       1640       1650       1660       1670
GAAAAgTTCC TcAAGTTCTG GgCtGTGACA TTCgAGATGC TGCCCACTGT
```

FIG. 2f

```
         .1660       .1670       .1680       .1690       .1700
         *   *       *   *       *   *       *   *       *   *
     GACCAGCGCG  GGGGCCAGCC  TGCTGCCCCC  CGAGGACAAC  TCTCAGGCCA
            1680        1690              1700        1710
       ----G-GTTG  GTGACCACAC  -T---CCCCC  TGAGGATGAC  TCAGAGGCTG

.1710       .1720       .1730       .1740       .1750
         *   *       *   *       *   *       *   *       *   *
     GCCCCGTGCC  CCCAGCGGAC  AACTCCGGGG  CTCCCACCGA  ACCCTCTGCG
    1720        1730        1740        1750        1760
    CCCCCGTCCC  ACCTACAGAC  GACTCCCAGG  GTGGTCCTGT  CCCACCTACA

.1760       .1770       .1780       .1790       .1800
         *   *       *   *       *   *       *   *       *   *
     GGTGACTCTG  AGGTGGCTCA  GATGCCTGTC  GTCATTGGTT  TCTAATGTCC
    1770        1780        1790        1800        1810
    GATGACTCTC  AGACAACACC  GGTGC-CCCC  AACAGACAAC  TCTC-AGGCT

.1810       .1820       .1830       .1840      .1850
         *   *       *   *       *   *       *   *      *   *
     TTGGCCTCCA  GGGGCCACAG  GAGACCCCAG  GGCCCACTTC  CCTCCCAAGT
    1820        1830        1840        1850        1860
    GGTGAC-TCT  GTGGAGG-CT  CAGATGCCTG  GTCCCATTGG  CTTCTAAAG-

.1860       .1870      .   *
         *   *       *   *
     GCCTCCTGAA  TAAAGCCTCA  ACCATCTC(POLY A)
    1870
    TCC-TATAAA  CCGGGGC
```

DNA ENCODING BOVINE PANCREATIC CHOLESTEROL ESTERASE

This is a division of application Ser. No. 08/350,501, filed Dec. 6, 1994, which is a continuation of U.S. application Ser. No. 07/856,910, filed May 12, 1992, now abandoned, which claims priority to PCT/US90/06483, filed Nov. 13, 1990, which in turn is a continuation of U.S. application Ser. No. 07/434,899, filed Nov. 13, 1989, now U.S. Pat. No. 5,173,408.

BACKGROUND OF THE INVENTION

1. Field of the Invention

The invention relates to enzymes involved in the metabolism of cholesterol and more specifically to the cholesterol esterase secreted by the pancreas in mammals. Cholesterol metabolism is of critical interest to those involved in protecting human health. Atherosclerosis is the leading cause of death in the United States and reduction of serum cholesterol levels has recently been embraced as a national health priority. See NIH Consensus Panel Report, J.A.M.A. 253:2094 (1985). NIH recommendations include measurement of serum cholesterol in all adults, with efforts to reduce cholesterol in those individuals with levels above 200 mg %. In this regard front line therapy is a reduction in the amount of cholesterol and triglycerides ingested, followed by the use of agents that interfere with absorption of ingested lipids. See Consensus Full Report, Arch. Inst. Med. 148:36 (1988).

Pancreatic cholesterol esterase plays a pivotal role in the absorption of cholesterol and fatty acids. The inhibition of cholesterol esterase could lead to reduced serum cholesterol levels. Numerous approaches to developing inhibitors of cholesterol esterase will likely be attempted, including the use of chemical inhibitors. Therapeutic biologicals, such as monoclonal or polyclonal antibodies to pancreatic cholesterol esterase have great potential. In particular, antibodies against purified cholesterol esterase can be isolated from the milk of immunized cows and used as an ingestible therapeutic. Analogs of pancreatic cholesterol esterase are proteins similar to cholesterol esterase, but with sufficient variation in amino acid sequence to bind cholesterol esters without releasing free cholesterol and fatty acids. If such analogs can be developed they will serve as powerful inhibitors of cholesterol esterase function.

Whatever type of inhibitor is being developed, large quantities of highly purified enzyme are required to test the efficacy of any potential inhibitor, as well as to better understand the enzyme and thus allow the development of further therapeutic means. There is, therefore, a need for methods to purify useful quantities of homogeneous pancreatic cholesterol esterase. In addition, for the preparation of analog inhibitors, the amino acid sequence of the enzyme and its underlying DNA sequence must be known. Thus, there is a need for a cloned DNA sequence encoding cholesterol esterase, from which the DNA and amino acid sequences may be determined.

Finally, pancreatic cholesterol esterase has considerable commercial utility for enzymatic hydrolysis or synthesis of ester linkages in the preparation of biologicals or foodstuffs such as dairy products. There is, therefore, a need for a means of producing commercially significant, large-scale quantities of homogeneous cholesterol esterase, especially from cows, which cannot be met by purification of the enzyme from natural sources. What is needed, then, is a means for producing pancreatic cholesterol esterase through the use of recombinant DNA expression vectors in a suitable host cell or organism, as well as a means of large-scale purification of the enzyme so expressed.

2. Information Disclosure

Borja et al., 1964, Proc. J. Exp. Biol. and Med. 116: 496, teach that cholesterol esterase is secreted by the pancreas, and that its catalysis of cholesterol ester hydrolysis to produce free cholesterol and free fatty acids is essential for the absorption of cholesterol. Bosner et al., 1988, Proc. Natl. Acad. Sci. USA 85: 7438, teach that cholesterol esterase performs its function while anchored to the intestinal membrane via a receptor-like interaction with brush border membrane associated heparin. Lange and Spilburg, in co-pending application U.S. Ser. No. 340,868, teach sulfated polysaccharide inhibitors of human pancreatic cholesterol esterase which are effective in blocking the absorption of cholesterol and fatty acids into intestinal cells.

Numerous procedures for the preparation of pancreatic cholesterol esterase have been reported. See, e.g. Allain et al., 1974, Clin. Chem. 20: 470, Calame et al., 1975, Arch. Biochem. Byophys. 168: 57, Labow et al., 1983, Biochem. Byophys. Acta 749: 32. In general, the reported procedures are tedious and give poor yields of heterogeneous material. Production of significant quantities of homogeneous material has not been achieved. For example, the commercially available cholesterol esterase, prepared by the method of Allain et al., is less than 5% pure according to both physical and functional assays. None of the existing preparative procedures has been useful for purifying cholesterol esterase from several different mammalian species.

SUMMARY OF THE INVENTION

The present invention is directed toward the preparation of useful quantities of homogeneous mammalian pancreatic cholesterol esterase. The invention encompasses methods for large-scale purification of pancreatic cholesterol esterase from natural sources or from prokaryotic or eukaryotic cell cultures producing recombinant mammalian pancreatic cholesterol esterase. The invention also comprises mammalian pancreatic cholesterol esterases purified according to such methods, and the use of such purified enzymes to produce and purify antibodies to such enzymes, and to screen potential inhibitors to such enzymes. In addition, the invention comprises the use of such purified enzyme to alter the cholesterol composition of food-stuffs and biologics.

The invention further comprises cloned DNA sequences encoding mammalian pancreatic cholesterol esterase, expression vectors containing such DNA sequences, and prokaryotic or eukaryotic cell cultures harboring said expression vectors, whereby said cell cultures are capable of producing mammalian pancreatic cholesterol esterase. The invention additionally comprises a process for commercial-scale production and purification of mammalian pancreatic cholesterol esterase through the application of the aforementioned purification methods to the supernatants of said mammalian pancreatic cholesterol esterase-producing cell cultures. The invention finally comprises homogeneous mammalian pancreatic cholesterol esterase produced by such a process.

BRIEF DESCRIPTION OF THE DRAWINGS

FIG. 1. The deduced amino acid sequence of bovine pancreatic cholesterol esterase.

FIG. 2. The cDNA sequence of bovine pancreatic cholesterol esterase. The underlined region of the cholesterol esterase cDNA is the complementary sequence of the oligonucleotide probe.

DETAILED DESCRIPTION OF THE INVENTION

Large-scale purification to homogeneity of mammalian pancreatic cholesterol esterase from human, bovine, porcine, and rat pancreas has now been achieved through the use of sulfated matrices in affinity chromatography. This is the first method ever to allow purification of this enzyme from all mammalian species tested. The major form of the enzyme purified from bovine pancreas has a molecular weight of 72 kilodaltons (kDa) and has never before been detected.

The observation that certain sulfated polysaccharides can decrease cholesterol absorption was recently disclosed in co-pending application U.S. Ser. No. 340,868, which is incorporated herein by reference. The sulfated polysaccharides reported in that investigation have the characteristic of binding to mammalian pancreatic cholesterol esterase. Thus, it is possible to use these compounds as an affinity matrix for the purification of pancreatic cholesterol esterase. Pancreatic cholesterol esterase contains a specific sulfate recognition site which allows it to bind to a large number of sulfated compounds which include, but are not limited to, heparin-agarose, Mono S, SP-Sephadex, cellulose sulfate, pectin sulfate, chitin sulfate, chitosan sulfate and 2, 3, or 6-congeners of chitosan sulfate, agar sulfate, amylopectin sulfate and any combination of monomers or polymers of the above. Those skilled in the art will recognize that other polysaccharides or resins may become sulfated through the action of chlorosulfate, sulfur dioxide, or other sulfating agents, whereby in view of the above, such sulfated polysaccharides or resins could be employed as affinity matrices for the purification of pancreatic cholesterol esterase. Preferably, sulfated polysaccharides are used as the affinity matrix. In particular, sulfated cellulose which has been sulfated to an extent insufficient to make it soluble in water or heparin agarose are most preferred.

The binding of sulfated polysaccharides by pancreatic cholesterol esterase involves one or more specific regions of the protein, one of which in the bovine protein is represented by the amino acid sequence MDGHLFATVDVPAID-KAKQDV. Those skilled in the art will recognize that the sulfate binding sites of the human, procine, and rat pancreatic cholesterol esterase enzymes, and of mammalian pancreatic cholesterol esterase enzymes will have substantially the same amino acid sequence. Substantially the same amino acid sequence is understood to mean an amino acid sequence in which any amino acid substitutions are conservative and do not significantly affect the function of the protein or any domain or region thereof (e.g., the ability of the region described above to bind to sulfated polysaccharides).

Specific amino acid sequences that bind sulfated agents have been identified by chemical cross-linking between the amino acid sequence and the sulfated agent, followed by cleavage of the protein to obtain the sulfated agent-bound oligopeptide and determination of the amino acid sequence of the oligopeptide. An oligopeptide having the amino acid sequence KKRCLQ has been identified as a binding site for sulfated agents on bovine rat and human cholesterol esterase. Binding of sulfated agents to this site on the enzyme does not inhibit enzyme function. In contrast, the oligopeptide PAINKGNKKV from human pancreatic cholesterol esterase binds sulfated agents in a manner that inhibits enzyme function. This binding site is only partially formed in the rat and bovine cholesterol esterases and comprises, respectively, the amino acid sequence PAID KAKQDV or PAINSNKQDV. The inhibitory binding sequence is encoded in the human gene by the nucleotide sequence CCTGCCATCAACAAGGGCAACAA-GAAAGTC.

Those skilled in the art will recognize that the oligopeptides of the invention are useful in various applications. For example, the oligopeptides may be used in in vitro binding assays to determine their capacity to bind to various sulfated agents. In this way, sulfated agents with a high binding affinity for the oligopeptides, and thus a high potential for binding or binding and inhibiting the enzyme can be identified. Any such sulfated agents would be useful for purifying the enzyme, and those binding the oligopeptide associated with enzyme inhibition will be strong candidates for cholesterol esterase inhibitor development. Thus the oligopeptides of the invention are useful for identifying agents that are useful for purifying or inhibiting pancreatic cholesterol esterase. The oligopeptides of the invention are also useful for therapeutic treatments designed to decrease cholesterol absorption. This is because the oligopeptides are capable of displacing the enzyme from its intestinal cell binding site by competitive binding. Thus the oligopeptides may be incorporated in a pharmaceutically acceptable carrier and administered in an amount effective for reducing cholesterol absorption. Displacement of cholesterol esterase by the oligopeptides may also be useful for enzyme purification purposes by using the oligopeptides to release bound enzyme in affinity chromatography procedures.

Purification of the enzyme takes advantage of the affinity of the enzyme, principally through its sulfate binding site, for a sulfated matrix. A solution comprising the pancreatic cholesterol esterase is applied to the sulfated matrix. The solution must be provided at a salt concentration and pH sufficient to allow the pancreatic cholesterol esterase to bind to the sulfated matrix. A variety of low salt concentrations will allow binding. Most preferably, binding is allowed to occur in 22 mM acetate, 50 mM benzamidine at a pH of 5.1. The use of a buffer at this pH and the presence of benzamidine serve to inhibit proteolysis. Prior art procedures have failed to address the problem of proteolysis during purification. This is believed to be the reason that the major form (72 kDa) of the bovine enzyme has never been detected previously, even though it may be related structurally as a derivative of the previously described 67 kDa bovine enzyme.

After binding of the pancreatic cholesterol esterase to the sulfated matrix has occurred, contaminating proteins can be removed by washing the column with a solution at a salt concentration and pH sufficient to allow continued binding of the pancreatic cholesterol esterase to the sulfated matrix. This may be achieved through the use of either a single wash solution or a linear salt gradient. For example, sulfated resins are preferably washed with linear salt gradients, whereas sulfated polysaccharides, including cellulose-sulfate and heparin-agarose are most preferably washed with a single wash solution at a higher salt concentration because these matrices bind the enzyme with higher affinity. Pancreatic cholesterol esterase is finally eluted from the sulfated matrix by washing the matrix with a solution at a salt concentration and pH sufficient to inhibit the binding of the enzyme to the sulfated matrix. When a linear salt gradient is employed, fractions are collected and the enzyme will be present in fractions at higher salt concentrations. Alternatively, when sulfated polysaccharides are utilized as the affinity matrix, the enzyme can be collected with a single wash utilizing a solution of a sulfated bile salt, such as taurocholate. Preferred sulfated matrices with conditions for binding and elution are described in Example 5. Combinations of matrices can be used for purification to homogeneity and other preliminary steps may be included. The bovine major (72 kDa) species, for example, was purified by the sequential chromatography steps of S-Sepharose with a linear salt gradient. SP-Sephadex with a linear salt gradient and mono-S with a linear salt gradient. Human pancreatic cholesterol esterase, in contrast, was preliminarily fractionated over hydroxylapatite and AcA-34, followed by purification on heparin-sepharose with a single high salt elution step.

The ability to purify to homogeneity significant quantities of mammalian pancreatic cholesterol esterases in general and human pancreatic cholesterol esterase in particular, allows for the first time on a large scale the production of antibodies to human pancreatic cholesterol esterase in particular, allows for the first time on a large scale the production of antibodies to human pancreatic cholesterol esterase, as well as to other mammalian pancreatic cholesterol esterase. The homogeneous enzyme is used to immunize cows which produce antibodies to the enzyme and secrete it into their milk. The antibodies are readily purified from the milk by affinity chromatography using a binding component comprising homogeneous pancreatic cholesterol esterase cross-linked to an inert matrix. In this manner large quantities of purified antibodies highly specific for pancreatic cholesterol esterase are readily prepared. Such antibodies, particularly antibodies to human pancreatic cholesterol esterase, can be used as inhibitors to pancreatic cholesterol esterase and might lead to reduced serum cholesterol levels.

FIG. 1 shows the amino acid sequence deduced from the nucleotide sequence shown in FIG. 2 of voice pancreatic cholesterol esterase. The amino acid sequence in FIG. 1 further enables the production of antibodies to peptides comprising less than a complete pancreatic cholesterol esterase molecule. Such peptides may be prepared by chemical synthesis or by proteolytic or chemical cleavage of the purified enzyme. The peptides may be used alone to immunize cows or may be coupled to a carrier protein, such as keyhole limpet hemocyanin (KLH). In either case the antibodies would be purified from cow's milk using affinity chromatography with the purified enzyme as the binding component, as described above.

The present invention provides, for the first time, useful quantities of homogeneous pancreatic cholesterol esterase. Thus the homogeneous enzyme composition can be used to screen potential inhibitors of pancreatic cholesterol esterase for their ability to modify enzyme properties, such as release of free cholesterol from fatty acyl cholesterol esters, or binding of immobilized heparin.

The ability to produce useful quantities of this enzyme in pure form further allows for the use of the enzyme in commercial applications. In particular, the purified enzyme will be used to alter the cholesterol/cholesterol ester composition of foodstuffs and biologics through its catalytic function. The bile salt taurocholate is required at concentrations above 1 mM for esterase activity whereas in the absence of taurocholate or in the present of low concentrations of taurocholate (i.e., less than 250 µM) the enzyme will operate to esterify cholesterol. Thus, both increases and decreases in free cholesterol in biologics or foodstuffs may be moderated by the same enzyme by simply altering the conditions.

The present invention provides also, for the first time, a composition of homogeneous mammalian pancreatic cholesterol esterase, especially the bovine 72 kDa species, in sufficient quantity for amino acid sequence analysis. Those skilled in the art will recognize that the ability to carry out such an analysis greatly enhances the probability of successfully cloning the gene encoding the underlying peptide sequence. Amino acid sequence determination allows the determination of a finite set of nucleotide sequences which can encode a particular peptide, based upon the genetic code. Within such a finite set of nucleotide sequences will be found a smaller set of nucleotide sequences which are more likely to encode the particular peptide, on the basis of the codon usage preference of the organism from which the gene is to be isolated.

Once a tissue source which expresses the protein of interest has been identified, mRNA can be isolated from this source. The mRNA can be used to synthesize cDNA, from which a library can be prepared. A mixture of oligonucleotides corresponding to the subset of nucleotide sequences most likely to encode a peptide from the protein can then be used to screen the library for the presence of a cDNA encoding the protein of interest.

In the case of mammalian pancreatic cholesterol esterase, the pancreas has long been known in the art as the tissue source expressing this enzyme. We have additionally discovered that expression of this enzyme in the pancreas of adult cows greatly exceeds that of calf pancreas. Thus, mRNA was prepared from adult bovine pancreas by standard procedures well known in the art. A cDNA library was prepared by conventional methods.

Conventional N-terminal amino acid sequence analysis of the homogeneous composition of bovine pancreatic cholesterol esterase, prepared as described herein, allowed the synthesis of a mixed oligonucleotide probe of the following sequence:

```
   A
5'- GCCTTCCACAAAGCCGCCTTCGGTATACAC-3'
   T   C      G       C       G
   C
```

This probe mixture was shown to hybridize very strongly in Northern blots of mRNA isolated from adult bovine pancreas to an mRNA species of 1.9 kb. No detectable hybridization was observed when mRNA isolated from calf pancreas was used. The probe was then used to identify a hybridizing clone from the cDNA library. The clone was isolated and a plasmid containing a full-length cDNA encoding pancreatic cholesterol esterase was excised therefrom. The nucleotide sequence of the cDNA was determined according to procedures well known in the art. The amino acid sequence for the entire bovine protein is shown in FIG. 1, as deduced from the nucleotide sequence shown in FIG. 2. The predicted peptide sequence is 578 amino acids in length and has a molecular weight of 63.5 kDa in the absence of glycosylation. There are two potential N-glycosylation sites. The theoretical isoelectric point of the unglycosylated protein is 5.1.

The cDNA shown in FIG. 2 was then used as a probe to screen a human pancreatic cDNA library. The bovine probe was hybridized to the human pancreatic cDNA library. Positive clones were obtained, including full length clones. Partial DNA sequence analysis confirmed that the clones encoded human pancreatic cholesterol esterase.

Thus, the present invention encompasses a cloned DNA sequence encoding mammalian pancreatic cholesterol esterase. For purposes of defining this aspect of the invention, a cloned DNA sequence will be interpreted to mean a DNA molecule comprising two portions: a (1) specific nucleotide sequence, covalently attached to (2) another DNA molecule portion which is capable of autonomous replication within a bacterial, yeast, plant, insect or mammalian cell, wherein the autonomously replicating DNA molecule is not a bacterial, yeast, plant, insect or mammalian chromosome, and whereby the cloned DNA sequence and attached autonomously replicating DNA molecule are capable of replicating autonomously as a unit within a bacterial, yeast, plant, insect or mammalian cell. Thus, a cloned DNA sequence may refer to a cloning vector that contains a specific nucleotide sequence encoding a cholesterol esterase. A DNA sequence encoding mammalian pancreatic cholesterol esterase is defined as a DNA sequence which, when transcribed and translated in a cell will give rise to a protein which is capable of releasing oleic acid from cholesteryl oleate, and is also capable of liberating palmitic acid from palmitoyl lysophosphatidyl choline. A representative DNA sequence encoding a mammalian pancreatic cholesterol esterase is the bovine sequence shown in FIG. 2. Those skilled in the art will recognize that the disclosure relating to the cloning of this DNA sequence coupled with the DNA sequence shown in FIG. 2 fully enables the cloning of other mammalian pancreatic cholesterol esterases including those from humans, pigs, and rats. DNA sequences encoding any mammalian pancreatic cholesterol esterase, as defined above are enabled and contemplated by the present invention.

A recombinant expression vector encoding a mammalian pancreatic cholesterol esterase can readily be prepared by methods well known in the art. Such a vector comprises the DNA sequence encoding a mammalian pancreatic cholesterol esterase, a promoter of other DNA sequence recognized by RNA polymerase as a signal for the initiation of transcription, and an origin of replication which allows the vector to replicate in a bacterial, yeast, plant, insect, or mammalian cell.

Cell culture expression systems have been extensively discussed in the art. Most preferred are mammalian cell culture expression systems, particularly the systems involving CHO(dhfr-) cells. In such a system, a recombinant expression vector encoding and capable of expressing the pancreatic cholesterol esterase can be introduced into CHO (dhfr-) cells together with 3 plasmid encoding and capable of expressing dhfr. Transfected cells can be selected in selective media, for example hypoxanthine-glycine-thymidine (HGT) media. Subsequent amplification of transfected DNA can be mediated by growing transfected cells in media containing methotrexate. Expression may be assayed by activity assays carried out using culture supernantants or through well established immunological procedures.

The following examples are shown by way of illustration and not by way of limitation.

EXAMPLE 1

Purification of Human Pancreatic Cholesterol Esterase

Human pancreas was received at autopsy. About 30 g of tissue in 10 mM phosphate, pH 6.0, 50 mM benzamidine, 0.5% digitonion were homogenized with a polytron, centrifugally pelleted (48,000 X g, 30 min.) and the supernatant collected. The supernatant was centrifugally pelleted (100,000 X g, 60 min.) again and the second supernatant was passed through glass wool and dialized overnight against 50 mM benzamidine, 10 mM phosphate, pH 6.8. The dialysate was loaded onto a hydroxylapatite column (2.6×10 cm) equilibrated with 50 mM benzamidine, 10 mM phosphate, pH 6.8. The column was washed with identical buffer, then developed with a linear gradient of 50 mM to 350 mM phosphate, pH 6.8, 50 mM benzamidine. The cholesterol esterase activity eluted at a conductivity of 20–22 mS/cm. These fractions were pooled and loaded onto an AcA34 column (Bio-Rad Laboratories, Inc., 2200 Wright Avenue, Richmond, Calif. 94804) (2.6×90 cm) equilibrated with 500 mM NaCl. 10 mM phosphate, pH 6.0. The fraction emerging at an apparent molecular weight of 350 kDa contained cholesterol esterase activity and was dialyzed against 10 mM phosphate, pH 6.0.

The enzyme was applied to heparin Sepharose (Pharmacia Inc., 800 Centennial Avenue, Piscataway, N.J. 08854) equilibrated with the same buffer. The resin was then washed with five to 10 column volumes of 50 mM NaCl, 50 mM benzamidine, 10 mM Tris, pH 7.2 followed by two column volumes of 20 mM taurocholate, 30 mM NaCl, 50 mM benzamidine, 10 mM Tris, pH 7.2. Purified enzyme is then eluted in 500 mM NaCl, 10 Tris, pH 7.2, 50 mM benzamidine.

EXAMPLE 2

Purification of Bovine Pancreatic Cholesterol Esterase

Commercially available bovine pancreatic cholesterol esterase (Sigma Chemical Co., P.O. Box 14509, St. Louis, Mo. 63178; purity<1%) in 10 mM Tris, pH 7.2, was applied to heparin-Sepharose (Pharmacia Inc., 800 Centennial Avenue, Piscataway, N.J. 08854) 1.5× 10 cm) equilibrated with the same buffer. The resin was developed further by washing with 0.10M NaCl, 10 mM Tris, pH 7.2. Little or no activity was found in any of these preliminary steps, even though virtually all of the applied protein was eluted. When the absorbance at 280 nm returned to zero, the resin was washed with 20 mM sodium taurocholate containing sodium chloride to give a conductivity of 13 to 15 mS/cm, the same conductivity as that of the previous washing buffer. All the activity was eluted in several fractions. This single purification step typically provided a 60 to 80% yield with a 50- to 100-fold purification and gives a single band at 67 kDa on SDS-PAGE. No additional activity was found when the resin was washed with higher concentrations of salt and the resin could be regenerated by washing with 2.0M NaCl, 10 mM Tris, pH 7.2. The large purification factor achieved by this single step indicates that heparin is acting as an affinity ligand for cholesterol esterase, a property demonstrated further by using different elution conditions. Thus, when the charged resin was washed with heparin (2 mg/ml), greater than 95% of the enzyme was eluted from the resin, while chondroitin sulfate (5 mg/ml); another sulfated mucopolysaccharide, removed less than 2% of bound enzyme.

EXAMPLE 3

Purification of Porcine Pancreatic Cholesterol Esterase

The same procedure described in Example 2 for the human enzyme was used for porcine pancreatic cholesterol esterase. In this case, active enzyme was found at 15 to 17 mS/cm from the hydroxylapatite column, and emerged from the AcA 34 gel filtration column (Bio-Rad Laboratories, 2200 Wright Avenue, Richmond, Calif. 94804) at a molecular weight of 81 kDa. This procedure provides homogeneous enzyme with molecular weight 81 kDa in 25% yield.

EXAMPLE 4

Purification of Bovine 72 kDa Major Species Pancreatic Cholesterol Esterase

Supernatant from bovine pancreas homogenate was prepared according to Example 1 as described for the human enzyme. The supernatant was chromatographed over S-Sepharose (Pharmacia Inc., 800 Centennial Avenue, Piscataway, N.J. 08854) in 25 mM acetate pH 5.1, 50 mM benzamidine. The enzyme was eluted from the column using a linear salt gradient from 175 mM NaCl to 500 mM NaCl. The eluate was loaded onto a SP-Sephadex (Pharmacia Inc., 800 Centennial Avenue, Piscataway, N.J. 08854) column in 25 mM acetate, pH 5.1, 50 mM benzamidine, then eluted with a linear gradient of 0 mM to 120 mM NaCl. The eluate contained two bands exhibiting cholesterol esterase activity, one at 72 kDa (90–99%) and one at 67 kDa (1–10%). The 72kDa form was completely separated from the 67 kDa form by chromatography over a mono-S column (Pharmacia Inc., 800 Centennial Avenue, Piscataway, N.J. 08854).

EXAMPLE 5

Purification of Cholesterol Esterases Using Sulfated Cellulose Columns

A. Preparation of Sulfated Cellulose Columns

Cellulose was lightly sulfated to maintain its insolubility and this material was used as a potent matrix for isolating and purifying the enzyme. Thus, 2.5 g of cellulose (type 100) was suspended in 50 ml water and 12.5 g of sulfur trioxide puridine complex were added with stirring. After one hour at room temperature, 100 ml of dimethylformamide were added, and the mixture was stirred for an additional 30 minutes. The cellulose sulfate was collected by centrifugation. After washing six times with water, the resin was packed in a small column (0.9×9 cm)

Resins such as those described in part A of this example and the other sulfated polysaccharides can be used to purify cholesterol esterases. For example, bovine cholesterol esterase was pumped onto the resin i 25 mM acetate, pH 5.1 and 15 ml/hr. All the activity was bound, but in this case, binding was so strong that even 2M NaCl in 25 mM acetate, pH 5.1 did not remove the enzyme. Elution with 100 mM taurocholate, a sulfated bile salt, removed all the activity in virtually 100% yield. Heparin agarose also functions as an effective affinity matrix for cholesterol esterase in the same manner.

EXAMPLE 6

Assays for Cholesterol Esterase Activity

Cholesterol esterase activity was determined by measuring the release of $[^{14}C]$-oleic acid from vesicles containing cholesteryl 1-$[^{14}C]$-oleic. Vescicles were prepared by drying under nitrogen a solution of 1.00 ml of 1.33 mM egg phosphatidylcholine in hexane and 1.27 ml of 1 mM cholesteryl oleate containing 10 µl of chloesteryl 1-$[^{14}C]$-oleate ($2.2\times10^5$ cpm) in chloroform. The precipitate was resuspended in 10 ml of 0.15M Tris, pH 7.5, vortexed vigorously for several seconds and then sonicated on ice for 20 minutes under nitrogen. Following sonication, the preparation was centrifuged at 48,000 X g for 60 minutes, and the vesicle preparation was carefully decanted and stored at 4° C. In a typical assay, 75 µl of cholesteryl $[^{14}C]$-oleate vesicles, 25 µl of 100 mM taurocholate, 175 µl of 0.15M Tris, pH 7.5 were mixed in a test tube and hydrolysis was initiated by adding 25 µl of enzyme to the reaction mixture at 37° C. After a known time, usually five minutes, the reaction was quenched by addition of 600 µl of 0.3N NaOH and 3 ml of benzene:methanol:chloroform (1:1.2:0.5). After mixing, the samples were centrifuged and 1 ml of the clear organic phase was removed and counted for radioactivity. Since only part of the sample was removed for counting, an efficiency sample was prepared by adding 100 µl of $[^{14}C]$-oleic acid vesicles of known specific radioactivity to 200 µl of 0.15M Tris, pH 7.5. The same manipulations were performed on this sample as those described above for assay. The efficiency of transfer was then determined by dividing the number of counts in the 1 ml organic phase by the dpm in 100 µl of starting $[^{14}C]$-oleic acid vesicles. Activity is expressed as nanomoles of oleic acid released/ml/hour and was less than 0.1 nmol/ml/hr in the absence of added enzyme. To assess the potential inhibition of chemical compounds, these agents are added to the incubation mixture before addition of cholesterol esterase and the ratio of $[^{14}C]$-oleate release determined as above and compared to the ratio observed in the absence of the test compound.

EXAMPLE 7

Preparation of Rabbit IgG Fraction Against 67 kDa Bovine Pancreatic Cholesterol Esterase Five hundred micrograms of homogeneous 67 kDa protein were emulsified in Freund's complete adjuvant (CFA) and injected subcutaneously into a New Zealand White rabbit. Twenty-one days later the rabbit was boosted with intraperitoneal injections of 250 µg protein dissolved in 1 ml of 10 mM sodium phosphate, 150 mM NaCl, pH 7.1. The rabbits was bled 10 days later and the presence of anti-cholesterol IgG was determined on Ouchterlony plates. Rabbit IgG was purified by passing 20 ml of rabbit serum over a protein A Sepharose (Pharmacia, Inc., 800 Centennial Avenue, Piscataway, N.J. 08854) column equilibrated with 20 mM Tris, 20 mM NaCl, pH 8.0. The resin was washed with equilibration buffer followed by 20 mM Tris, 0.5% deoxycholate, 500 mM NaCl, pH 8.0 and then equilibration buffer. Finally, the IgG was eluted with 100 mM glycine pH 2.8. Similarly, 2 mg of homogeneous human cholesterol esterase emulsified in CFA are injected into four subcutaneous sites in a cow, and booster injections of 1 mg protein at three and six weeks are made Secretory antibodies are elicited in the cow's milk that are directed at human cholesterol esterase and can be separated from other milk proteins by ammonium sulfate precipitation and ion exchange chromatography.

EXAMPLE 8

Construction and Screening of Bovine Pancreas cDNA Library

A. Construction of Bovine Pancreas cDNA Library

Total RNA was extracted from bovine pancreas with 5.5M guanidine thiocyanate, as described by Han et al., 1987, Biochemistry 26: 1617–1625; poly $A^+$ RNA was purified from total RNA by chromatography on oligo dT-cellulose (Pharmacia Inc., 800 Centennial Avenue, Piscataway, N.J. 08854). A cDNA library was constructed using 5 µg of twice-selected poly $A^+$ RNA using a Pharmacia cDNA synthesis kit according to the method of Gubler and Hoffman, 1983, Gene, 25: 263–269. The EcoRI-ended double-stranded cDNA was ligated into EcoRI-digested and dephosphorylated λ-ZAP vector arms (Stratagene, 11099 North Torrey Pines Road, La Jolla, Calif. 92037), and packaged using a Stratagene kit. About 300,000 to 500,000 independent, recombinant clones were obtained.

B. Preparation of Probe for Screening the cDNA Library

Total RNA and poly $A^+$ were isolated from pancreas of adult cow or calf as described in part A of this example. RNA was denatured with formaldehyde and formamide and electrophoreses on a 1% agarose-formaldehyde gel containing 2.2M formaldehyde. RNA was transferred by capillary action to a nylon membrane (Schleicher and Schuell, Inc., 10 Optical Avenue, Keene, N.H. 03431) in 20 X SSPE. A 30-mer probe mixture was synthesized based upon N-terminal amino acid sequence determined from purified bovine pancreatic cholesterol esterase. The probe mixture:

```
      A
5'- GCCTTCCACAAAGCCGCCTTCGGTATACAC-3'
      T  C      G          C     G
      C
``` was labelled using $\alpha$-$[^{32}P]$-ATP and polynucleotide kinase. The probe mixture hybridized strongly to a single 1.9 kb band in lanes containing total RNA or poly $A^+$ RNA from adult bovine pancreas, but did not hybridize to lanes containing total RNA or poly $A^+$ RNA from calf pancreas.

C. Screening Bovine Pancreas cDNA Library

The radiolabelled probe described in part B of this example was used to probe the cDNA library constructed as described in part A of this example. The library was screened by plaque hybridization in the presence of 0.25% nonfat dry milk in 6 X SSPE. Prehybridization and hybridization were conducted at 60° C. A bluescript plasmid was excised from the hybridizing λ-ZAP clones by co-infecting XLI-Blue cells with positive λ-ZAP phage and R-408 helper phage. Excision from the plasmid of a cDNA clone encoding the entire cholesterol esterase protein was performed, with identification in the cDNA sequence of both the N-terminal protein sequence and the sequence of the 30mer probe given in part B of this example. Bluescript plasmids were harvested by the alkaline lysis method of Birnboin, 1983, Meth. Enzymol, 100: 243–255.

EXAMPLE 9

DNA Sequence Analysis of cDNA for Cholesterol Esterase

Each sequencing reaction used approximately 3 µl of double-stranded pBluescript plasmid with positive inserts and 50 ng of sequencing primer. Double-stranded plasmid was denatured for 5 minutes at room temperature with 0.2M NaOH, 0.2 mM ethylene diamine tetraacetate (EDTA) (final concentrations); DNA was precipitated with 0.18M ammonium acetate, pH 5.4 (final concentration) and 2.5 volumes of ethanol. The mixture was chilled on dry ice for 15 minutes and the DNA pellet was spun down for 10 minutes in a microfuge. The pellets were washed with 70% ethanol and vacuum dried. The inserts were sequenced by the dideoxy chain termination method of Sanger et. al., 1977, Proc. Natl. Acad. Sci. USA 74: 5463–5467 using Sequenase™ 2.0 (U.S. Biochemical Corporation, P. O. Box 22400, Cleveland, Ohio 44122) or AMV reverse transcriptase sequencing kit (Stratagene, 11099 North Torrey Pines Road, La Jolla, Calif 92037). Internal sequences for both strands were obtained by sequential nested primers, 18 to 20 nucleotides in length. The DNA sequence thus obtained is shown in FIG. 2.

EXAMPLE 10

Construction of Expression Vectors

The eukaryotic-prokaryotic shuttle vector pSV2neo has been described by Southern and Berg, (1982) J. Mol. App. Genet. 2: 327–341. A vector capable of expressing bovine pancreatic cholesterol esterase in mammalian cells is prepared by inserting the full-length cDNA (FIG. 2) isolated as described in Example 8, into pSV2neo in such a way as to replace the neo gene, and thus be flanked by the SV-40 early promoter upstream and the SV-40 polyadenylation signal downstream. The insert in the cDNA clone is first site-directed mutagenized to remove a single EcoRI restriction site within the cDNA and then the insert is removed by digesting the cDNA clone with EcoRI. The 1.9 kb insert is isolated by electroelution. The EcoRI ends are converted to blunt ends by incubation of the DNA fragment in the presence of Klenow polymerase and 10 µm dNTPS for 5 minutes. The neo gene is removed from pSV2neo by digestion with HindIII and SmaI and the 4.4 kb vector fragment is isolated by electroelution. The HindIII end is converted to a blunt end using Klenow polymerase. The isolated and blunt-ended fragments are then digested together by the use of T4 DNA ligase and T4RNA ligase (10:1 unit ratio) in the presence of 100 µm ATP and 50 mM $MgCl_2$ at room temperature for about three hours. A portion of the ligation mixture is used to transform competent HB101 E. coli bacteria, which are selected for ampicillin resistance. The orientation of the insert is determined by DNA sequencing, as described in Example 9.

EXAMPLE 11

Expression of Bovine Pancreatic Cholesterol Esterase in CHO cells

The expression vector described in Example 10 is co-introduced into DHFR deficient CHO cells along with a plasmid expressing the DHFR gene, by the method of Graham and Van der Eb, 1973, J. Virology 52: 456–467. The plasmid expressing DHFR is prepared as described in Example 10, except that the DHFR gene from the plasmid pE342.HBV,E400.D22 is used in place of the bovine pancreatic cholesterol esterase gene. The plasmid pE342.HBV.E400.D22 is described in U.S. Pat. No. 4,850,330. Transfected cells are selected in HGT medium. Resistant colonies are tested for expression of pancreatic cholesterol esterase by collecting their media supernatants and utilizing them in the assay described in Example 6. Clones found to be expressing cholesterol esterase are seeded at 200,000 cells per 100 nM plate in 50 mM methoxtrexate (MTX) to select for DNA amplification. Cells surviving the initial MTX selection are tested again for cholesterol esterase activity. Those cells showing an increase in cholesterol esterase activity, relative to pre-amplification activity levels, are then further selected for amplification in 500 nM MTX. Resistant cells showing additional increases in cholesterol esterase activity are finally selected for optimum amplification in 10,000 nM MTX. Those subclones resistant to 10,000 nM MTX which produce the highest levels of cholesterol esterase activity are used as producer cell lines to provide cholesterol esterase which, after purification as described in Example 4, can be used to screen for enzyme inhibitors, produce anti-enzyme antibodies or alter the cholesterol/cholesterol ester composition of foodstuffs.

EXAMPLE 12

Synthesis of Cholesterol Esters by Cholesterol Esterase

Bovine pancreatic cholesterol esterase was incubated at pH 6.0 with 900 µm $^{14}C$-oleate and 700 µm cholesterol or with cholesteryl-$[^{14}C]$-oleate, at varying concentrations of the bile salt taurocholate. Ester synthesis in the former case was assayed by determining the rate of formation of cholesteryl-$[^{14}C]$-oleate and in the latter case as described in Example 6. The synthesis and hydrolytic rates and the ratios between them at various concentrations of taurocholate are shown below in Table I. Rates are expressed as µmoles of product formed per mg of enzyme per hour.

TABLE I

|  | Taurocholate, mM | | | |
| --- | --- | --- | --- | --- |
|  | 0 | 0.1 | 1.0 | 10.0 |
| Synthetic | 0.83 | 14.2 | 32.5 | 78.3 |
| Hydrolytic | 0 | 0 | 12.0 | 73.5 |
| Ratio+ | — | — | 2.7 | 1.1 |

These results indicate that the enzyme can be made to act primarily as a synthetic enzyme at appropriate concentrations of taurocholate below 1 mM. Thus, the enzyme can be used to alter the cholesterol/cholesterol ester composition of a given solution by simply adding enzyme and adjusting the level of taurocholate from 0 to 1 mM. Above 1 mN taurocholate, the enzyme is useful for the general hydrolysis of cholesterol esters. Thus, free cholesterol in foodstuffs such as liquid dairy products can be converted into esterified cholesterol, which may be more poorly absorbed than free cholesterol or whose absorption may be inhibited through the ingestion of sulfated polysaccharides (see, for example, U.S. Ser. Nos. 340,868, 425,109 and co-pending U.S. application entitled, "The Use of Sulfated Polysaccharides To Decrease Cholesterol and Fatty Acid Absorption", filed Oct. 31, 1989, all of which are hereby incorporated by reference).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A DNA sequence comprising a nucleotide sequence encoding a bovine pancreatic cholesterol esterase.

2. A DNA sequence according to claim 1 wherein the nucleotide sequence encoding the bovine pancreatic cholesterol esterase comprises a nucleotide sequence shown in FIG. 2 (SEQ ID NO. 2).

3. A cloning vector comprising a nucleotide sequence encoding a bovine pancreatic cholesterol esterase.

4. A recombinant expression vector comprising the DNA sequence of claim 1, wherein the vector is capable of expressing bovine pancreatic cholesterol esterase in a transformed eukaryotic or prokaroyotic cell culture.

5. A prokaryotic cell culture transformed with the expression vector of claim 4, wherein the transformed prokaryotic cell culture is capable of expressing bovine pancreatic cholesterol esterase.

6. A eukaryotic cell culture transformed with the expression vector of claim 4, wherein the transformed eukaryotic cell culture is capable of expressing bovine pancreatic cholesterol esterase.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 597 amino acids
( B ) TYPE: amino acid
( D ) TOPOLOGY: linear ( i i ) MOLECULE TYPE: protein ( i x ) FEATURE:
( A ) NAME/KEY: misc_feature
( B ) LOCATION: 1..597
( D ) OTHER INFORMATION: /note= "Bovine pancreatic cholesterol esterase"

( x i ) SEQUENCE DESCRIPTION: SEQ ID NO:1:

```
Leu Gly Ala Ser Arg Leu
 1               5

Gly Pro Ser Pro Gly Cys Leu Ala Val Ala Ser Ala Ala Lys Leu Gly
            10              15                  20

Ser Val Tyr Thr Glu Gly Gly Phe Val Glu Gly Val Asn Lys Lys Leu
        25              30              35

Ser Leu Phe Gly Asp Ser Val Asp Ile Phe Lys Gly Ile Pro Phe Ala
    40              45              50

Ala Ala Pro Lys Ala Leu Glu Lys Pro Glu Arg His Pro Gly Trp Gln
55              60              65                      70

Gly Thr Leu Lys Ala Lys Ser Phe Lys Lys Arg Cys Leu Gln Ala Thr
                75              80              85

Leu Thr Gln Asp Ser Thr Tyr Gly Asn Glu Asp Cys Leu Tyr Leu Asn
            90              95              100

Ile Trp Val Pro Gln Gly Arg Lys Glu Val Ser His Asp Leu Pro Val
        105             110             115

Met Ile Trp Ile Tyr Gly Gly Ala Phe Leu Met Gly Ala Ser Gln Gly
    120             125             130

Ala Asn Phe Leu Ser Asn Tyr Leu Tyr Asp Gly Glu Glu Ile Ala Thr
135             140             145             150

Arg Gly Asn Val Ile Val Val Thr Phe Asn Tyr Arg Val Gly Pro Leu
                155             160             165
```

```
Gly Phe Leu Ser Thr Gly Asp Ser Asn Leu Pro Gly Asn Tyr Gly Leu
            170             175             180
Trp Asp Gln His Met Ala Ile Ala Trp Val Lys Arg Asn Ile Glu Ala
            185             190             195
Phe Gly Gly Asp Pro Asp Asn Ile Thr Leu Phe Gly Glu Ser Ala Gly
            200             205             210
Gly Ala Ser Val Ser Leu Gln Thr Leu Ser Pro Tyr Asn Lys Gly Leu
215             220             225             230
Ile Lys Arg Ala Ile Ser Gln Ser Gly Val Gly Leu Cys Pro Trp Ala
            235             240             245
Ile Gln Gln Asp Pro Leu Phe Trp Ala Lys Arg Ile Ala Glu Lys Val
            250             255             260
Gly Cys Pro Val Asp Asp Thr Ser Lys Met Ala Gly Cys Leu Lys Ile
            265             270             275
Thr Asp Pro Arg Ala Leu Thr Leu Ala Tyr Lys Leu Pro Leu Gly Ser
            280             285             290
Thr Glu Tyr Pro Lys Leu His Tyr Leu Ser Phe Val Pro Val Ile Asp
295             300             305             310
Gly Asp Phe Ile Pro Asp Asp Pro Val Asn Leu Tyr Ala Asn Ala Ala
            315             320             325
Asp Val Asp Tyr Ile Ala Gly Thr Asn Asp Met Asp Gly His Leu Phe
            330             335             340
Val Gly Met Asp Val Pro Ala Ile Asn Ser Asn Lys Gln Asp Val Thr
            345             350             355
Glu Glu Asp Phe Tyr Lys Leu Val Ser Gly Leu Thr Val Thr Lys Gly
            360             365             370
Leu Arg Gly Ala Asn Ala Thr Tyr Glu Val Tyr Thr Glu Pro Trp Ala
375             380             385             390
Gln Asp Ser Ser Gln Glu Thr Arg Lys Lys Thr Met Val Asp Leu Glu
            395             400             405
Thr Asp Ile Leu Phe Leu Ile Pro Thr Lys Ile Ala Val Ala Gln His
            410             415             420
Lys Ser His Ala Lys Ser Ala Asn Thr Tyr Thr Tyr Leu Phe Ser Gln
            425             430             435
Pro Ser Arg Met Pro Ile Tyr Pro Lys Trp Met Gly Ala Asp His Ala
            440             445             450
Asp Asp Leu Gln Tyr Val Phe Gly Lys Pro Phe Ala Thr Pro Leu Gly
455             460             465             470
Tyr Arg Ala Gln Asp Arg Thr Val Ser Lys Ala Met Ile Ala Tyr Trp
            475             480             485
Thr Asn Phe Ala Arg Thr Gly Asp Pro Asn Thr Gly His Ser Thr Val
            490             495             500
Pro Ala Asn Trp Asp Pro Tyr Thr Leu Glu Asp Asp Asn Tyr Leu Glu
            505             510             515
Ile Asn Lys Gln Met Asp Ser Asn Ser Met Lys Leu His Leu Arg Thr
            520             525             530
Asn Tyr Leu Gln Phe Trp Thr Gln Thr Tyr Gln Ala Leu Pro Thr Val
535             540             545             550
Thr Ser Ala Gly Ala Ser Leu Leu Pro Pro Glu Asp Asn Ser Gln Ala
            555             560             565
Ser Pro Val Pro Pro Ala Asp Asn Ser Gly Ala Pro Thr Glu Pro Ser
            570             575             580
Ala Gly Asp Ser Glu Val Ala Gln Met Pro Val Val Ile Gly Phe
```

(2) INFORMATION FOR SEQ ID NO:2:

(i) SEQUENCE CHARACTERISTICS:
    (A) LENGTH: 1907 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 100..129
    (D) OTHER INFORMATION: /note= "complementary sequence to oligonucleotide probe"

(ix) FEATURE:
    (A) NAME/KEY: CDS
    (B) LOCATION: 1..1824

(ix) FEATURE:
    (A) NAME/KEY: misc_feature
    (B) LOCATION: 1..1907
    (D) OTHER INFORMATION: /note= "Bovine pancreatic cholesterol esterase cDNA"

(ix) FEATURE:
    (A) NAME/KEY: sig_peptide
    (B) LOCATION: 1..30

(ix) FEATURE:
    (A) NAME/KEY: mat_peptide
    (B) LOCATION: 31..1821

(xi) SEQUENCE DESCRIPTION: SEQ ID NO:2:

| GCC | TAG | AGG | CAG | ACA | CTG | ACT | ATG | GGG | CGG | CTG | GGA | GCT | AGC | CGT | CTT | 48 |
|---|---|---|---|---|---|---|---|---|---|---|---|---|---|---|---|---|
| Ala | * | Arg | Gln | Thr | Leu | Thr | Met | Gly | Arg | Leu | Gly | Ala | Ser | Arg | Leu | |
| -10 | | | | -5 | | | | 1 | | | | | 5 | | | |

| GGG | CCG | TCG | CCT | GGC | TGC | TTG | GCA | GTA | GCG | AGT | GCA | GCG | AAG | TTG | GGC | 96 |
|---|---|---|---|---|---|---|---|---|---|---|---|---|---|---|---|---|
| Gly | Pro | Ser | Pro | Gly | Cys | Leu | Ala | Val | Ala | Ser | Ala | Ala | Lys | Leu | Gly | |
| | | | 10 | | | | | 15 | | | | | 20 | | | |

| TCC | GTA | TAC | ACC | GAA | GGC | GGC | TTC | GTG | GAG | GGC | GTC | AAC | AAG | AAG | CTG | 144 |
|---|---|---|---|---|---|---|---|---|---|---|---|---|---|---|---|---|
| Ser | Val | Tyr | Thr | Glu | Gly | Gly | Phe | Val | Glu | Gly | Val | Asn | Lys | Lys | Leu | |
| | | 25 | | | | | 30 | | | | | 35 | | | | |

| AGC | CTC | TTT | GGC | GAC | TCT | GTT | GAC | ATC | TTC | AAG | GGC | ATC | CCC | TTC | GCT | 192 |
|---|---|---|---|---|---|---|---|---|---|---|---|---|---|---|---|---|
| Ser | Leu | Phe | Gly | Asp | Ser | Val | Asp | Ile | Phe | Lys | Gly | Ile | Pro | Phe | Ala | |
| | 40 | | | | | 45 | | | | | 50 | | | | | |

| GCC | GCC | CCC | AAG | GCC | CTG | GAG | AAG | CCC | GAG | CGA | CAC | CCC | GGC | TGG | CAA | 240 |
|---|---|---|---|---|---|---|---|---|---|---|---|---|---|---|---|---|
| Ala | Ala | Pro | Lys | Ala | Leu | Glu | Lys | Pro | Glu | Arg | His | Pro | Gly | Trp | Gln | |
| 55 | | | | | 60 | | | | | 65 | | | | | 70 | |

| GGG | ACC | CTG | AAG | GCC | AAG | AGC | TTT | AAG | AAA | CGG | TGC | CTG | CAG | GCC | ACG | 288 |
|---|---|---|---|---|---|---|---|---|---|---|---|---|---|---|---|---|
| Gly | Thr | Leu | Lys | Ala | Lys | Ser | Phe | Lys | Lys | Arg | Cys | Leu | Gln | Ala | Thr | |
| | | | | 75 | | | | | 80 | | | | | 85 | | |

| CTC | ACG | CAG | GAC | AGC | ACC | TAC | GGA | AAT | GAA | GAC | TGC | CTC | TAC | CTC | AAC | 336 |
|---|---|---|---|---|---|---|---|---|---|---|---|---|---|---|---|---|
| Leu | Thr | Gln | Asp | Ser | Thr | Tyr | Gly | Asn | Glu | Asp | Cys | Leu | Tyr | Leu | Asn | |
| | | | 90 | | | | | 95 | | | | | 100 | | | |

| ATC | TGG | GTC | CCC | CAG | GGC | AGG | AAG | GAA | GTC | TCC | CAC | GAC | CTG | CCC | GTC | 384 |
|---|---|---|---|---|---|---|---|---|---|---|---|---|---|---|---|---|
| Ile | Trp | Val | Pro | Gln | Gly | Arg | Lys | Glu | Val | Ser | His | Asp | Leu | Pro | Val | |
| | | 105 | | | | | 110 | | | | | 115 | | | | |

| ATG | ATC | TGG | ATC | TAT | GGA | GGC | GCC | TTC | CTC | ATG | GGG | GCC | AGC | CAA | GGG | 432 |
|---|---|---|---|---|---|---|---|---|---|---|---|---|---|---|---|---|
| Met | Ile | Trp | Ile | Tyr | Gly | Gly | Ala | Phe | Leu | Met | Gly | Ala | Ser | Gln | Gly | |
| | 120 | | | | | 125 | | | | | 130 | | | | | |

| GCC | AAC | TTT | CTC | AGC | AAC | TAC | CTC | TAC | GAC | GGG | GAG | GAG | ATT | GCC | ACA | 480 |
|---|---|---|---|---|---|---|---|---|---|---|---|---|---|---|---|---|
| Ala | Asn | Phe | Leu | Ser | Asn | Tyr | Leu | Tyr | Asp | Gly | Glu | Glu | Ile | Ala | Thr | |
| 135 | | | | | 140 | | | | | 145 | | | | | 150 | |

| CGG | GGC | AAC | GTC | ATC | GTG | GTC | ACG | TTC | AAC | TAC | CGC | GTT | GGG | CCC | CTG | 528 |

|  |  |  |  |  |  |  |  |  |  |  |  |  |  |  |  |
|---|---|---|---|---|---|---|---|---|---|---|---|---|---|---|---|
| Arg | Gly | Asn | Val | Ile<br>155 | Val | Val | Thr | Phe | Asn<br>160 | Tyr | Arg | Val | Gly | Pro<br>165 | Leu |

| GGC | TTT | CTC | AGC | ACC | GGG | GAC | TCC | AAC | CTG | CCA | GGT | AAC | TAT | GGC | CTT | 576 |
|---|---|---|---|---|---|---|---|---|---|---|---|---|---|---|---|---|
| Gly | Phe | Leu | Ser<br>170 | Thr | Gly | Asp | Ser<br>175 | Asn | Leu | Pro | Gly | Asn<br>180 | Tyr | Gly | Leu | |

| TGG | GAT | CAG | CAC | ATG | GCC | ATT | GCT | TGG | GTG | AAG | AGG | AAC | ATT | GAG | GCC | 624 |
| Trp | Asp | Gln | His<br>185 | Met | Ala | Ile | Ala | Trp<br>190 | Val | Lys | Arg | Asn | Ile<br>195 | Glu | Ala | |

| TTC | GGA | GGA | GAC | CCC | GAC | AAC | ATC | ACC | CTC | TTT | GGG | GAG | TCG | GCC | GGA | 672 |
| Phe | Gly | Gly<br>200 | Asp | Pro | Asp | Asn | Ile<br>205 | Thr | Leu | Phe | Gly | Glu<br>210 | Ser | Ala | Gly | |

| GGC | GCC | AGC | GTC | TCT | CTG | CAG | ACC | CTC | TCT | CCC | TAC | AAC | AAG | GGC | CTC | 720 |
| Gly | Ala | Ser<br>215 | Val | Ser | Leu | Gln<br>220 | Thr | Leu | Ser | Pro | Tyr<br>225 | Asn | Lys | Gly | Leu<br>230 | |

| ATC | AAG | CGA | GCC | ATC | AGC | CAG | AGT | GGA | GTG | GGT | TTG | TGC | CCT | TGG | GCC | 768 |
| Ile | Lys | Arg | Ala | Ile<br>235 | Ser | Gln | Ser | Gly | Val<br>240 | Gly | Leu | Cys | Pro | Trp<br>245 | Ala | |

| ATC | CAG | CAG | GAC | CCC | CTC | TTC | TGG | GCT | AAA | AGG | ATT | GCA | GAG | AAG | GTG | 816 |
| Ile | Gln | Gln | Asp<br>250 | Pro | Leu | Phe | Trp | Ala<br>255 | Lys | Arg | Ile | Ala | Glu<br>260 | Lys | Val | |

| GGC | TGC | CCC | GTG | GAC | GAC | ACC | AGC | AAG | ATG | GCT | GGG | TGT | CTG | AAG | ATC | 864 |
| Gly | Cys | Pro<br>265 | Val | Asp | Asp | Thr | Ser<br>270 | Lys | Met | Ala | Gly | Cys<br>275 | Leu | Lys | Ile | |

| ACT | GAC | CCC | CGT | GCC | CTG | ACG | CTG | GCC | TAT | AAG | CTG | CCC | CTG | GGA | AGC | 912 |
| Thr | Asp<br>280 | Pro | Arg | Ala | Leu | Thr<br>285 | Leu | Ala | Tyr | Lys | Leu<br>290 | Pro | Leu | Gly | Ser | |

| ACG | GAA | TAC | CCC | AAG | CTG | CAC | TAT | CTG | TCC | TTC | GTC | CCC | GTC | ATC | GAT | 960 |
| Thr<br>295 | Glu | Tyr | Pro | Lys | Leu<br>300 | His | Tyr | Leu | Ser | Phe<br>305 | Val | Pro | Val | Ile | Asp<br>310 | |

| GGA | GAC | TTC | ATC | CCT | GAT | GAC | CCC | GTC | AAC | CTG | TAC | GCC | AAC | GCC | GCG | 1008 |
| Gly | Asp | Phe | Ile | Pro<br>315 | Asp | Asp | Pro | Val | Asn<br>320 | Leu | Tyr | Ala | Asn | Ala<br>325 | Ala | |

| GAC | GTC | GAC | TAC | ATA | GCG | GGC | ACC | AAT | GAC | ATG | GAC | GGC | CAC | CTC | TTT | 1056 |
| Asp | Val | Asp | Tyr<br>330 | Ile | Ala | Gly | Thr | Asn<br>335 | Asp | Met | Asp | Gly | His<br>340 | Leu | Phe | |

| GTC | GGG | ATG | GAC | GTG | CCA | GCC | ATC | AAC | AGC | AAC | AAA | CAG | GAC | GTC | ACG | 1104 |
| Val | Gly | Met<br>345 | Asp | Val | Pro | Ala | Ile<br>350 | Asn | Ser | Asn | Lys | Gln<br>355 | Asp | Val | Thr | |

| GAG | GAG | GAC | TTC | TAT | AAG | CTG | GTC | AGC | GGG | CTC | ACC | GTC | ACC | AAG | GGG | 1152 |
| Glu | Glu<br>360 | Asp | Phe | Tyr | Lys | Leu<br>365 | Val | Ser | Gly | Leu | Thr<br>370 | Val | Thr | Lys | Gly | |

| CTC | AGA | GGT | GCC | AAT | GCC | ACG | TAC | GAG | GTG | TAC | ACC | GAG | CCC | TGG | GCC | 1200 |
| Leu<br>375 | Arg | Gly | Ala | Asn | Ala<br>380 | Thr | Tyr | Glu | Val | Tyr<br>385 | Thr | Glu | Pro | Trp | Ala<br>390 | |

| CAG | GAC | TCA | TCC | CAG | GAG | ACC | AGG | AAG | AAG | ACC | ATG | GTG | GAC | CTG | GAG | 1248 |
| Gln | Asp | Ser | Ser | Gln<br>395 | Glu | Thr | Arg | Lys | Lys<br>400 | Thr | Met | Val | Asp | Leu<br>405 | Glu | |

| ACT | GAC | ATC | CTC | TTC | CTG | ATC | CCC | ACA | AAG | ATT | GCC | GTG | GCC | CAG | CAC | 1296 |
| Thr | Asp | Ile | Leu | Phe<br>410 | Leu | Ile | Pro | Thr | Lys<br>415 | Ile | Ala | Val | Ala | Gln<br>420 | His | |

| AAG | AGC | CAC | GCC | AAG | AGC | GCC | AAC | ACC | TAC | ACC | TAC | CTG | TTC | TCC | CAA | 1344 |
| Lys | Ser | His | Ala<br>425 | Lys | Ser | Ala | Asn | Thr<br>430 | Tyr | Thr | Tyr | Leu | Phe<br>435 | Ser | Gln | |

| CCG | TCT | CGG | ATG | CCC | ATC | TAC | CCC | AAG | TGG | ATG | GGG | GCT | GAC | CAC | GCC | 1392 |
| Pro | Ser | Arg<br>440 | Met | Pro | Ile | Tyr | Pro<br>445 | Lys | Trp | Met | Gly | Ala<br>450 | Asp | His | Ala | |

| GAT | GAC | CTC | CAG | TAT | GTC | TTC | GGG | AAG | CCC | TTC | GCC | ACC | CCC | CTG | GGC | 1440 |
| Asp | Asp<br>455 | Leu | Gln | Tyr | Val | Phe<br>460 | Gly | Lys | Pro | Phe | Ala<br>465 | Thr | Pro | Leu | Gly<br>470 | |

| TAC | CGG | GCC | CAA | GAC | AGG | ACT | GTG | TCC | AAG | GCC | ATG | ATT | GCC | TAC | TGG | 1488 |

-continued

| | | | | | | | | | | | | | | | |
|---|---|---|---|---|---|---|---|---|---|---|---|---|---|---|---|
| Tyr | Arg | Ala | Gln | Asp<br>475 | Arg | Thr | Val | Ser | Lys<br>480 | Ala | Met | Ile | Ala | Tyr<br>485 | Trp |

| ACC | AAC | TTT | GCC | AGA | ACT | GGG | GAC | CCT | AAC | ACG | GGC | CAC | TCG | ACA | GTG | 1536 |
|---|---|---|---|---|---|---|---|---|---|---|---|---|---|---|---|---|
| Thr | Asn | Phe | Ala<br>490 | Arg | Thr | Gly | Asp | Pro<br>495 | Asn | Thr | Gly | His | Ser<br>500 | Thr | Val | |

| CCC | GCA | AAC | TGG | GAT | CCC | TAC | ACC | CTG | GAA | GAT | GAC | AAC | TAC | CTG | GAA | 1584 |
|---|---|---|---|---|---|---|---|---|---|---|---|---|---|---|---|---|
| Pro | Ala | Asn<br>505 | Trp | Asp | Pro | Tyr | Thr<br>510 | Leu | Glu | Asp | Asp | Asn<br>515 | Tyr | Leu | Glu | |

| ATC | AAC | AAG | CAG | ATG | GAC | AGC | AAC | TCT | ATG | AAG | CTG | CAT | CTG | AGG | ACC | 1632 |
|---|---|---|---|---|---|---|---|---|---|---|---|---|---|---|---|---|
| Ile | Asn<br>520 | Lys | Gln | Met | Asp | Ser<br>525 | Asn | Ser | Met | Lys | Leu<br>530 | His | Leu | Arg | Thr | |

| AAC | TAC | CTG | CAG | TTC | TGG | ACC | CAG | ACC | TAC | CAG | GCC | CTG | CCC | ACG | GTG | 1680 |
|---|---|---|---|---|---|---|---|---|---|---|---|---|---|---|---|---|
| Asn<br>535 | Tyr | Leu | Gln | Phe | Trp<br>540 | Thr | Gln | Thr | Tyr | Gln<br>545 | Ala | Leu | Pro | Thr | Val<br>550 | |

| ACC | AGC | GCG | GGG | GCC | AGC | CTG | CTG | CCC | CCC | GAG | GAC | AAC | TCT | CAG | GCC | 1728 |
|---|---|---|---|---|---|---|---|---|---|---|---|---|---|---|---|---|
| Thr | Ser | Ala | Gly | Ala<br>555 | Ser | Leu | Leu | Pro | Pro<br>560 | Glu | Asp | Asn | Ser | Gln<br>565 | Ala | |

| AGC | CCC | GTG | CCC | CCA | GCG | GAC | AAC | TCC | GGG | GCT | CCC | ACC | GAA | CCC | TCT | 1776 |
|---|---|---|---|---|---|---|---|---|---|---|---|---|---|---|---|---|
| Ser | Pro | Val<br>570 | Pro | Pro | Ala | Asp | Asn<br>575 | Ser | Gly | Ala | Pro | Thr<br>580 | Glu | Pro | Ser | |

| GCG | GGT | GAC | TCT | GAG | GTG | GCT | CAG | ATG | CCT | GTC | GTC | ATT | GGT | TTC | TAATGTCC | 1831 |
|---|---|---|---|---|---|---|---|---|---|---|---|---|---|---|---|---|
| Ala | Gly | Asp<br>585 | Ser | Glu | Val | Ala | Gln<br>590 | Met | Pro | Val | Val | Ile<br>595 | Gly | Phe | | |

GGCCTCCAGG GGCCACAGGA GACCCCAGGG CCCACTTCCC TCCCAAGTGC CTCCTGAATA 1891

AAGCCTCAAC CATCTC 1907

( 2 ) INFORMATION FOR SEQ ID NO:3:

( i ) SEQUENCE CHARACTERISTICS:
        ( A ) LENGTH: 605 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Arg | Gln | Thr | Leu | Thr<br>- 5 | Met | Gly | Arg | Leu | Gly<br>1 | Ala | Ser | Arg | Leu<br>5 | |
| Gly | Pro | Ser | Pro<br>10 | Gly | Cys | Leu | Ala | Val<br>15 | Ala | Ser | Ala | Ala | Lys<br>20 | Leu | Gly |
| Ser | Val | Tyr<br>25 | Thr | Glu | Gly | Gly | Phe<br>30 | Val | Glu | Gly | Val | Asn<br>35 | Lys | Lys | Leu |
| Ser | Leu<br>40 | Phe | Gly | Asp | Ser | Val<br>45 | Asp | Ile | Phe | Lys | Gly<br>50 | Ile | Pro | Phe | Ala |
| Ala<br>55 | Ala | Pro | Lys | Ala | Leu<br>60 | Glu | Lys | Pro | Glu | Arg<br>65 | His | Pro | Gly | Trp<br>70 | Gln |
| Gly | Thr | Leu | Lys | Ala<br>75 | Lys | Ser | Phe | Lys | Lys<br>80 | Arg | Cys | Leu | Gln | Ala<br>85 | Thr |
| Leu | Thr | Gln | Asp<br>90 | Ser | Thr | Tyr | Gly | Asn<br>95 | Glu | Asp | Cys | Leu | Tyr<br>100 | Leu | Asn |
| Ile | Trp | Val<br>105 | Pro | Gln | Gly | Arg | Lys<br>110 | Glu | Val | Ser | His | Asp<br>115 | Leu | Pro | Val |
| Met | Ile<br>120 | Trp | Ile | Tyr | Gly | Gly<br>125 | Ala | Phe | Leu | Met | Gly<br>130 | Ser | Gly | Gln | Gly |
| Ala<br>135 | Asn | Phe | Leu | Lys | Asn<br>140 | Tyr | Leu | Tyr | Asp | Gly<br>145 | Glu | Glu | Ile | Ala | Thr<br>150 |
| Arg | Gly | Asn | Val | Ile<br>155 | Val | Val | Thr | Phe | Asn<br>160 | Tyr | Arg | Val | Gly | Pro<br>165 | Leu |

```
Gly  Phe  Leu  Ser   Thr  Gly  Asp  Ser   Asn  Leu  Pro  Gly   Asn  Tyr  Gly  Leu
               170                       175                  180

Trp  Asp  Gln  His   Met  Ala  Ile  Ala   Trp  Val  Lys  Arg   Asn  Ile  Glu  Ala
               185                       190                  195

Phe  Gly  Gly  Asp   Pro  Asp  Asn  Ile   Thr  Leu  Phe  Gly   Glu  Ser  Ala  Gly
               200                       205                  210

Gly  Ala  Ser  Val   Ser  Leu  Gln  Thr   Leu  Ser  Pro  Tyr   Asn  Lys  Gly  Leu
215                       220                       225                       230

Ile  Lys  Arg  Ala   Ile  Ser  Gln  Ser   Gly  Val  Gly  Leu   Cys  Pro  Trp  Ala
               235                       240                  245

Ile  Gln  Gln  Asp   Pro  Leu  Phe  Trp   Ala  Lys  Arg  Ile   Ala  Glu  Lys  Val
               250                       255                  260

Gly  Cys  Pro  Val   Asp  Asp  Thr  Ser   Lys  Met  Ala  Gly   Cys  Leu  Lys  Ile
               265                       270                  275

Thr  Asp  Pro  Arg   Ala  Leu  Thr  Leu   Ala  Tyr  Lys  Leu   Pro  Leu  Gly  Ser
               280                       285                  290

Thr  Glu  Tyr  Pro   Lys  Leu  His  Tyr   Leu  Ser  Phe  Val   Pro  Val  Ile  Asp
295                       300                       305                       310

Gly  Asp  Phe  Ile   Pro  Asp  Pro  Val   Asn  Leu  Tyr  Ala   Asn  Ala  Ala
               315                       320                  325

Asp  Val  Asp  Tyr   Ile  Ala  Gly  Thr   Asn  Asp  Met  Asp   Gly  His  Leu  Phe
               330                       335                  340

Val  Gly  Met  Asp   Val  Pro  Ala  Ile   Asn  Ser  Asn  Lys   Gln  Asp  Val  Thr
               345                       350                  355

Glu  Glu  Asp  Phe   Tyr  Lys  Leu  Val   Ser  Gly  Leu  Thr   Val  Thr  Lys  Gly
               360                       365                  370

Leu  Arg  Gly  Ala   Asn  Ala  Thr  Tyr   Glu  Val  Tyr  Thr   Glu  Pro  Trp  Ala
375                       380                       385                       390

Gln  Asp  Ser  Ser   Gln  Glu  Thr  Arg   Lys  Lys  Thr  Met   Val  Asp  Leu  Glu
               395                       400                  405

Thr  Asp  Ile  Leu   Phe  Leu  Ile  Pro   Thr  Lys  Ile  Ala   Val  Ala  Gln  His
               410                       415                  420

Lys  Ser  His  Ala   Lys  Ser  Ala  Asn   Thr  Tyr  Thr  Tyr   Cys  Phe  Ser  Gln
               425                       430                  435

Pro  Ser  Arg  Met   Pro  Ile  Tyr  Pro   Lys  Trp  Met  Gly   Ala  Asp  His  Ala
               440                       445                  450

Asp  Asp  Leu  Gln   Tyr  Val  Phe  Gly   Lys  Pro  Phe  Ala   Thr  Pro  Leu  Gly
455                       460                       465                       470

Tyr  Arg  Ala  Gln   Asp  Arg  Thr  Val   Ser  Lys  Ala  Met   Ile  Ala  Tyr  Trp
               475                       480                  485

Thr  Asn  Phe  Ala   Arg  Thr  Gly  Asp   Pro  Asn  Thr  Gly   His  Ser  Thr  Val
               490                       495                  500

Pro  Ala  Asn  Trp   Asp  Pro  Tyr  Thr   Leu  Glu  Asp  Asp   Asn  Tyr  Leu  Glu
               505                       510                  515

Ile  Asn  Lys  Gln   Met  Asp  Ser  Asn   Ser  Met  Lys  Leu   His  Leu  Arg  Thr
               520                       525                  530

Asn  Tyr  Leu  Gln   Phe  Trp  Thr  Gln   Thr  Tyr  Gln  Ala   Leu  Pro  Thr  Val
535                       540                       545                       550

Thr  Ser  Ala  Gly   Ala  Ser  Leu  Leu   Pro  Pro  Glu  Asp   Asn  Ser  Gln  Ala
               555                       560                  565

Ser  Pro  Val  Pro   Pro  Ala  Asp  Asn   Ser  Gly  Ala  Pro   Thr  Glu  Pro  Ser
               570                       575                  580

Ala  Gly  Asp  Ser   Glu  Val  Ala  Gln   Met  Pro  Val  Val   Ile  Gly  Phe
               585                       590                  595
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met  Asp  Gly  His  Leu  Phe  Ala  Thr  Val  Asp  Val  Pro  Ala  Ile  Asp  Lys
1                   5                        10                         15

Ala  Lys  Gln  Asp  Val
               20
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Lys  Lys  Arg  Cys  Leu  Gln
1                   5
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Pro  Ala  Ile  Asn  Lys  Gly  Asn  Lys  Lys  Val
1                   5                        10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Pro  Ala  Ile  Asp  Lys  Ala  Lys  Gln  Asp  Val
1                   5                        10
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
       Pro Ala Ile Asn Ser Asn Lys Gln Asp Val
       1               5                   10
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
CCTGCCATCA ACAAGGGCAA CAAGAAAGTC                                   30
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..30
        ( D ) OTHER INFORMATION: /note= "oligonucleotide probe
            mixture."

( x i ) SEQUENCE DESCRIPTION: SEQ ID NO:10:

```
NCCT Y CCACA ARGCCGCCTT CGG Y ATACAS                               30
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
       Lys Lys Arg Cys Leu Trp
       1               5
```